(12) United States Patent
Knapp et al.

(10) Patent No.: US 7,019,320 B2
(45) Date of Patent: Mar. 28, 2006

(54) LIQUID FILLED CONFORMAL WINDOWS AND DOMES

(75) Inventors: David J. Knapp, Tucson, AZ (US); Paul K. Manhart, Boulder, CO (US)

(73) Assignee: Raytheon Company, Waltham, MA (US)

(*) Notice: Subject to any disclaimer, the term of this patent is extended or adjusted under 35 U.S.C. 154(b) by 138 days.

(21) Appl. No.: 10/682,578

(22) Filed: Oct. 9, 2003

(65) Prior Publication Data

US 2005/0077489 A1  Apr. 14, 2005

(51) Int. Cl.
    *G02B 27/22* (2006.01)

(52) U.S. Cl. ........................... 250/573; 359/642
(58) Field of Classification Search ............. 235/462, 235/454, 467, 470, 472; 250/201, 568; 359/642
    See application file for complete search history.

(56) References Cited

U.S. PATENT DOCUMENTS 6,028,712 A * 2/2000 McKenney ............ 359/642
6,313,951 B1 * 11/2001 Manhart ............... 359/642

* cited by examiner

Primary Examiner—Thanh X. Luu
Assistant Examiner—Tony Ko
(74) Attorney, Agent, or Firm—Thomas J. Finn; Leonard A. Alkov; Karl A. Vick (57) ABSTRACT

A system for sensing light transmitted with reduced optical aberrations into the interior of an enclosure utilizing a liquid filled cavity. A window is disposed on the exterior surface of the enclosure for allowing light to pass into the enclosure. A lens is disposed on the interior side of the window, defining a cavity between the window and the lens. A fluid is disposed within that cavity. An optical sensor is disposed in the interior of the enclosure, and positioned to receive light through the window and the lens. The exterior surface of the window is shaped to conform to the exterior surface of the enclosure. The fluid is selected for having an index of refraction that minimizes the mismatch with the index of refraction of the window.

34 Claims, 6 Drawing Sheets

LIQUID FILLED CONFORMAL WINDOWS AND DOMES

BACKGROUND OF THE INVENTION

1. Field of the Invention

The present invention relates to optics. More specifically, the present invention relates to corrective optical elements used in conjunction with conformal windows and complex domes for protecting optical sensors.

2. Description of the Related Art

Optical sensors are employed in a variety of systems that are deployed into a variety of environments. Electro-optic sensors are commonly used, and may be designed to be sensitive in a variety of wavelengths, including visible light, near infrared, long infrared, as well as other wavelengths. Optical sensors are typically structured to detect energy along a focal plane onto which a real image is formed by an optical system placed between the focal plane of the sensor and some object field in the distant environment. Various operating environments are encountered, including air, water, fluids, chemicals, bodily fluids, and as well as other environments. For example, a guided missile operates in an ambient air environment and might employ a near infrared electro-optical sensor with an image field corresponding to distance objects in the environment, such as enemy aircraft. In another example, a submersible research vehicle might employ a visible light sensor that operates in seawater.

Electro-optical sensors typically cannot endure direct exposure to the environment in which they operate, so designers place an optical window between the sensor and the environment to protect the sensor. The optical window thus becomes an element of the optical system used with the sensor. Naturally, the optical system used with an optical sensor is a major factor in the resolving power and performance of the overall system. System designers often seek high optical performance. In order to minimize the optical aberrations that are contributed by the optical window, designers have typically chosen simple optical configurations for these windows, most commonly flat plates or hemispherical domes.

There are other considerations in system designs that employ electro-optical sensors with optical windows. For example, in the case of a missile, the aerodynamics of the missile in flight is of critical importance in the effectiveness of the missile system as a whole. The same is often true in other systems, including torpedoes, chemical process sensors, blood vessel sensors, and many other systems. In the case of a missile, the electro-optic sensor is preferably placed at the nose of the missile, which shape has a great effect on aerodynamic drag. A flat plate window is a poor aerodynamic choice, a hemispherical window is better, but an elongated shape is preferred to improve the drag coefficient of the missile. In other applications, such as where a sensor 'looks' out the side of a system built into a complex shaped enclosure, designers prefer that the optical window conform to the shape of the system enclosure. Such an optical window is called a conformal optical window.

The problem with complex shaped optical windows is that they induce optical aberrations that must be corrected in order to maintain high optical performance of the sensor system. What this has meant in the prior art is that systems designers have had to add one or more optical corrector elements to counteract the aberrations induced by the window. The window behaves as a lens, which refracts light according to the shape of the window, the indices or refraction of the window, the environment itself, and other components in the optical system in the sensor. While technology exists for building complex shaped windows and corresponding optical corrector elements, they are difficult to design, add to system cost, as well as increasing development time and effort. Thus, there is a need in the art for a systems and method for reducing the aberrations and deleterious effects of conformal and complex shaped optical windows used with optical sensors.

SUMMARY OF THE INVENTION

The need in the art is addressed by the systems and methods of the present invention. A system and method for sensing light transmitted with reduced optical aberrations into the interior of an enclosure is taught. A window is disposed on the exterior surface of the enclosure for allowing light to pass into the enclosure. A lens is disposed on the interior side of the window, defining a cavity between the window and the lens. A fluid is disposed within that cavity. An optical sensor is disposed in the interior of the enclosure, and positioned to receive light through the window and the lens.

In a specific embodiment, the exterior surface of the window is formed to a shape other than a flat plate or a spherical dome. In another embodiment, the exterior surface of the window is shaped to conform with the exterior surface of the enclosure. More generally, the exterior surface of the window may be formed to conform to a rotated-conic section selected from any of an ellipse, a parabola, or a hyperbola. Also, it may be formed as a rotated ogive shape.

In a specific embodiment, the fluid is selected for having an index of refraction that minimizes the mismatch with the index of refraction of the window. In particular, the fluid can have an index of refraction similar to the index of refraction of the window. In an illustrative embodiment, the fluid is water, which is beneficial in the case where the system operates under water. In a refinement of the invention, the fluid may be a gel. The system may operate in a fluid environment where the fluid has an index of refraction similar to the index of refraction of the fluid environment. Other environments are contemplated, which may be any of a bodily fluid, a hydrocarbon, a lubricant, or an industrial chemical. In a particular embodiment, the system is a torpedo.

In a specific embodiment, the lens is a corrector element formed to offset optical aberrations caused by the window and the fluid. The lens may be comprised of a single optical element. The sensor may be gimbal mounted to vary the look angle of the sensor. In an illustrative embodiment, the lens is particularly formed to correct optical aberrations created by the combination of the window and the fluid, such that light is coupled to the optical sensor in a diffraction-limited condition.

The present invention also teaches an underwater, system for sensing light transmitted with reduced optical aberrations into the interior of an enclosure. This system includes a conformal window disposed on the exterior surface of the enclosure for allowing light to pass into the enclosure. It also includes a single element corrector lens that is disposed on the interior side of the window, thereby defining a cavity between the window and the lens. The cavity is filled with water. A gimbal mounted optical sensor is disposed in the interior of the enclosure and positioned to receive light through the window and the lens through various look angles, which are possible with the gimbal mount. Also, the lens is formed to correct optical aberrations created by the combination of the window and the fluid, such that light is coupled to the optical sensor in a diffraction-limited condition.

The present invention also teaches a method of implementing a system for transmitting light with reduced optical aberrations to a sensor on the interior of an enclosure. The method includes the steps of disposing a window on the exterior surfaces of the enclosure, thereby allowing light to pass into the enclosure and, positioning a lens on the interior side of the window, thereby defining a cavity between the window and the lens. Next, filling the cavity with a fluid, and, then positioning the optical sensor in the interior of the enclosure to receive light through passing through the window and the lens.

In a refinement to the foregoing, the method further includes the step of forming the exterior surface of the window to a shape other than a flat plate or a spherical dome. In particular, conforming the exterior surface of the window to the shape of the exterior surface of the enclosure. The exterior surface of the window may be formed to conform to a rotated conic section selected from any of an ellipse, a parabola, or a hyperbola, or, it may be formed as a rotated ogive.

The fluid may be selected for having an index of refraction that minimizes the mismatch with the index of refraction of the window. In another embodiment, the fluid has an index of refraction similar to the index of refraction of the window. The fluid may be water. In such a case, the system may operate under water. The fluid may also be a gel. In a particular embodiment, the system operates in a fluid environment and the fluid has an index of refraction similar to the index of refraction of the fluid environment. The fluid environment may be a bodily fluid, a hydrocarbon, a lubricant, or an industrial chemical. In an illustrative embodiment, the system is a torpedo.

In a refinement of the method, the lens is a corrector element formed to offset optical aberrations caused by the window and the fluid. The lens may be comprised of a single optical element. In a specific embodiment of the method, the positioning step is accomplished with a gimbal mount, thereby varying the look angle of the sensor. The lens may be formed to correct optical aberrations created by the combination of the window and the fluid, such that light is coupled to the optical sensor in a diffraction limited-condition.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Optical windows used to protect optical sensors from an external environment are most commonly formed as flat plates of hemispherical domes because these shapes are relatively easy to design, test and build. However, when considering the shape of the enclosure in which the optical system is installed, and the other operational considerations of the system and enclosure, the flat and hemispherical shapes are often times less than optimum. Designers often prefer to use more complex shapes to either conform to the shape of the system enclosure, or to adapt the system shape to the dynamics of the system-operating environment. A window that conforms to the aerodynamics or fluid-dynamics requirements of a system, such as the exterior shape of an aircraft or a sea vessel is an example of a conformal window. Another example of a conformal window is one used at a leading edge or tip of a projectile that has been elongated for the purpose of reducing drag, such as a missile nose or torpedo nose. These complex shapes are collectively referred to as conformal shapes in that they either conform to the contours of the enclosure they are coupled to or conform to the dynamic requirements of the system, as opposed to merely addressing the optical design requirements alone.

Figure 1:
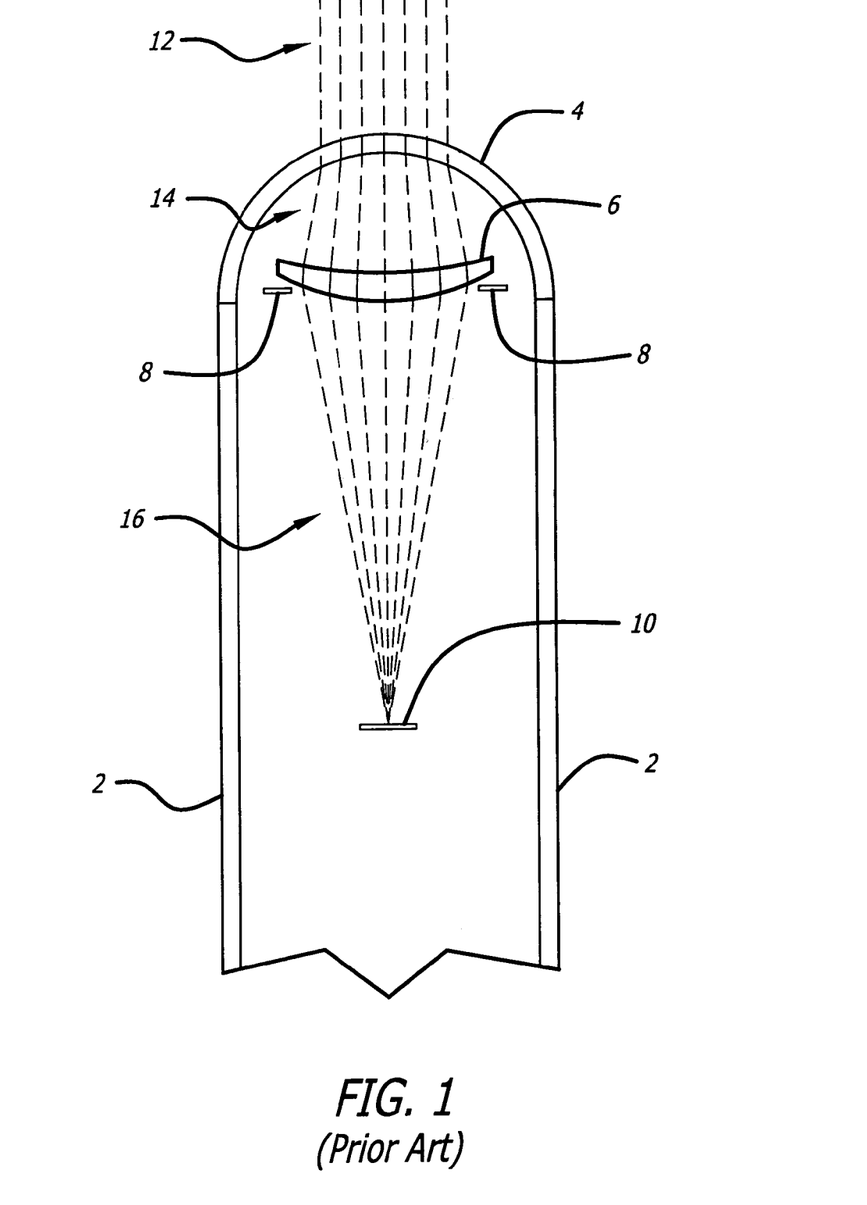
FIG. 1 is an optical diagram of a prior art hemispherical dome window and optical sensor system.

FIG. 1 is an optical diagram of a prior art hemispherical window and corrector lens used in an optical sensor system. An enclosure 2, such as a missile or torpedo housing is fitted with a hemispherical dome window 4. The dome 4 has even thickness and is relatively easy to fabricate and test. The bundle of light rays 12, incident upon the dome 4 from a distant object is refracted 14 as they pass through the dome 4. The degree of refraction is determined according to Snell's law, which is familiar to those skilled in the art. The parameters of the refraction calculations include the index of refraction of the external environment, the index of refraction of the dome 4 material, and the index of refraction of the interior space of the enclosure. In the case of a missile, in the prior art, these materials are air, glass, and air respectively. Various kinds of glass are available to designers, and are known to those skilled in the art. In the case of an underwater system such as a torpedo, these materials are water, glass, and air respectively. Again various kind of glass may be employed. The refraction of the bundle or rays 14 passing through the dome 4 is corrected and coupled to a sensor system. In FIG. 1, a conic plate corrector 6 is employed as a perfect lens. Conceptually, the prefect lens is used hereinafter to distinguish the dome and corrector elements of the optical elements that would be employed in the sensor itself. Those skilled in the art are familiar with various sensor configurations, most of which are designed for diffraction-limited performance. The teachings of the present invention are not directed to the sensor optical system, but rather the optical system used in front of the sensor to correct for optical aberrations induced by the conformal window or dome. Thus, in FIG. 1, the corrector element 6 is also a perfect lens that forms a real image on a focal plane array 10 of an electro-optical sensor. The bundle of light rays 14 is refracted by the lens 6, limited by an aperture stop 8, to converge 16 to form points of light on the focal plane array surface.

The hemispherical dome window also has an advantage in the case of a gimbal mounted optical sensor. With a gimbal mount, the sensor assembly can be rotated and pointed in directions away from the straight-ahead direction, sometimes referred to as the bore sight of the system. The deviation from straight ahead is referred to as the field of regard ('FOR'). With a hemispherical dome, the axis of rotation of the gimbal mount can be placed at the center of the hemispherical dome. Given that the dome has uniform thickness, there is no variation in the optical characteristics of the system as the optical sensor is rotated about the gimbal mount. This is an ideal system from a purely optical design perspective. However, as mentioned hereinbefore, the hemispherical dome is not the ideal shape form other design perspectives.

Considering the dynamics of a torpedo or missile nosepiece, those skilled in the art understand that drag is reduced by elongating the nose in the direction of travel of the device. The ratio of the length of the nose to the diameter is known as the fineness ratio. A 180 degree hemispherical dome has a fineness ratio of 0.5 and a drag coefficient of about 0.75 at Mach 2. By doubling the length of the dome, making it an elliptical shape, the fineness ration increases to 1.0 while the drag coefficient is reduced to about 0.45 at Mach 2. Going further, extending the nose to a fineness ratio of 1.5 drops the drag coefficient to about 0.33 at Mach 2. The drag coefficient is dependent on velocity. The foregoing drag coefficients were derived from the Engineering Sciences Data (Aeronautical Series): Item Number 80021. Thus, there is a significant reason to employ conformal windows and domes from a system dynamics perspective. The same is generally true in other kinds of conformal shapes, although the dynamics considerations may be more complex in the case of something like a canopy or side-looking window on a vehicle.

It is useful to design conformal optics in the shape of a conic section rotated about an axis, such as an ellipse rotated to an ellipsoid dome, a parabola rotated to a paraboloid, or a hyperbola rotated to a hyperboloid, and so forth. From an optical perspective, these are complex shapes because the angles and thickness of material that lights rays pass through change as rays are displaced from the central bore sight of the system. Then, considering the effect of a gimbal mounted optical sensor, the optical scenario is even more complex as the look angle of the sensor is rotated about the gimbal. Even greater optical challenges are created in the case of more complex dome shapes. An ogive is a good shape for a nose cone from a dynamics perspective, however, an ogive is a difficult shape to deal with from an optical perspective. Compound curves are often times found on the exterior surfaces of crafts and vessels, and it is frequently desirable to form conformal windows that follow such contours. The prior art has addressed the problems of correcting optical aberrations through the use of corrector lenses, mirrors and other devices. Correction of aberrations from conformal windows and domes has been performed using deformable mirrors, fixed correctors, arch optical elements, rotation of Zernike plates, and tilting or translating optical elements, and so forth. All of these corrective approaches are greatly affected by the magnitude of the aberration that must be corrected. Simply put, as the aberration increases, the complexity and design challenge commensurately increases. The correlary to this is that as aberrations increase, the cost of correcting them increases as well.

The advancement in the art contributed by the present invention is realized by addressing the magnitude of the aberrations created by a conformal window through minimization of the degree of refraction through the window. As noted, Snell's law determines the degree of refraction of lightrays as a function of several variables. Optical engineers use Snell's Law in optical corrector designs by controlling thickness, contours and materials of lenses and optical elements. The present invention minimizes the degree of aberrations by minimizing the magnitude of refraction. Under Snell's law, the magnitude of refraction is proportional to the difference in the refractive index of the two materials that form a boundary. For example, air has an index of refraction of about 1.0 and glass has an index of about 1.4. Thus, an air-glass-air lens refracts light according to a 1.0 to 1.4 transition, followed by a 1.4 to 1.0 transition. Water has an index of refraction of about 1.33. Thus, an underwater window follows a 1.33 to 1.4 to 1.0 lens transition (water-glass-air). A reduction in the aberrations is achieved according to the present invention by filling the backside of the lens with a fluid, such as water, that has an index of refraction closer to glass than air. In the case of an under water device, a water-glass-water transition results in an index of refraction transition of 1.33 to 1.4 to 1.33. The reduction in the magnitude of the refraction of the light rays results in an advantageous reduction in the degree of aberrations resulting from conformal domes or windows. This results in a less severe corrective element requirement and a correspondingly lower cost. In addition to simple fluids such as water, other fluids and gels can be used to address parameters including the index of refraction of the fluid or gel, thermal properties, as well as other physical properties of the fluid or gel.

The present invention projects the utility of conformal optics into the realm of electro-optical sensors for submerged platforms, such as torpedoes. Specifically, it teaches the use of filling the cavity behind a conformal window or dome with a fluid such as water to minimize the index mismatches between the water to dome to interior cavity interfaces. As a consequence of the reduced index mismatch, aberrations are minimized from the dome or window. This significantly reduces the complexity of designing conformal optics for submerged applications. This in turn allows a designer to utilize electro-optical sensors without impacting platform performance.

Figure 2:
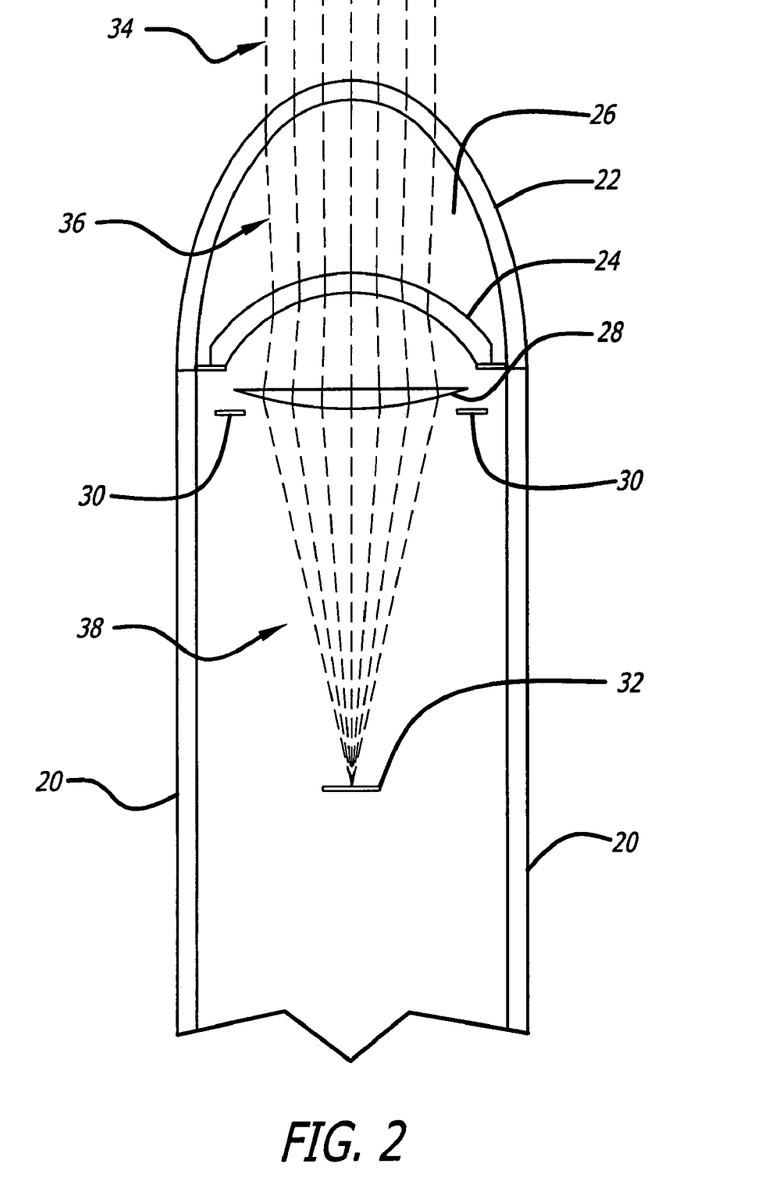
FIG. 2 is an optical diagram of an optical sensor system with a liquid filled conformal dome according to an illustrative embodiment of the present invention.

Reference is directed to FIG. 2, which is an optical diagram of a conformal window and optical sensor system according to an illustrative embodiment of the present invention. A bundle of light rays 34 from a distant object travel through water and are incident upon a conformal window 22 that is an ellipsoid with an improved fineness ratio. Thus, the index of refraction through the exterior surface of the dome results from a 1.33 to 1.4 index transition. On the interior side of the dome 22, an optical corrector element 24 is positioned to receive the light rays entering the system enclosure 20. The space between the dome 22 and the corrector element 24 defines a cavity 26 this is filled with fluid. In the illustrative embodiment, the fluid is water so the degree of refraction through the interior surface of the dome results from a 1.4 to 1.33 index transition. The design results in reduced refraction as compared to an air, or gas, filled cavity. The decrease in refraction angles is approximately one order of magnitude. Lower refraction results in lowered aberrations and less complex corrective requirements. The corrector element 24 controls the residual aberrations and couples the light rays to a perfect lens 28 and through an aperture stop 30 to be focused 38 on a focal plane 32 in the sensor. FIG. 1 illustrates a computer-modeled systems based on the aforementioned parameters and is capable of diffraction limited performance at the focal plane 32, with the use of a constant thickness dome 22 and single corrective lens element 24. To clearly illustrate the benefit of the present invention on the illustrative embodiment, a second computer model was processed and resulted in the performance illustrated in FIG. 2.

Figure 3:
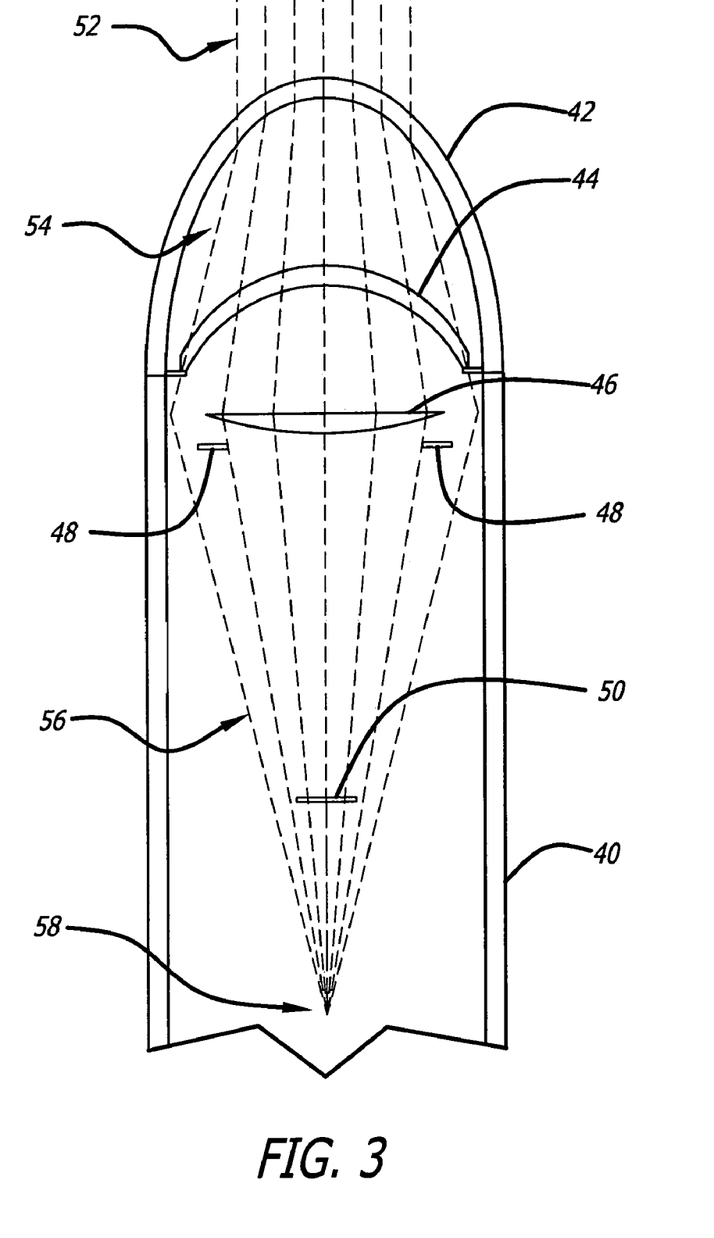
FIG. 3 is an optical diagram of an optical sensor system with an air filled conformal dome according to an illustrative embodiment of the present invention.

Reference is directed to FIG. 2, which is an optical diagram of the illustrative embodiment where an air filled cavity is employed instead of a liquid filled cavity. The system enclosure 40 has a conformal dome window 42 that is an ellipsoid as in FIG. 2. In FIG. 3, the same corrector lens 44 forms a cavity with the dome 42, however, the cavity is air filled so that the interior surface of the dome refracts according to a 1.4 to 1.0 index transition. Thus, the bundle of rays 52 is refracted through the dome and disperses at a much greater angle 54 than with the liquid filled cavity: The net effect is that the corrective element would be underdesigned and the rays diverging so much that the perfect lens is too small to gather and correctly focus the rays 56 on the focal plane 50. Rather, the rays focus at a point 58 beyond the focal plane 50. The problems present in FIG. 3 are corrected by filling the cavity between the dome 42 and the corrector element 44 with water. Those skilled in the art will realized that the dome and corrector element could be designed to properly illuminate the perfect lens and focal plane, but this is not possible without creating other design issues.

Figure 4:
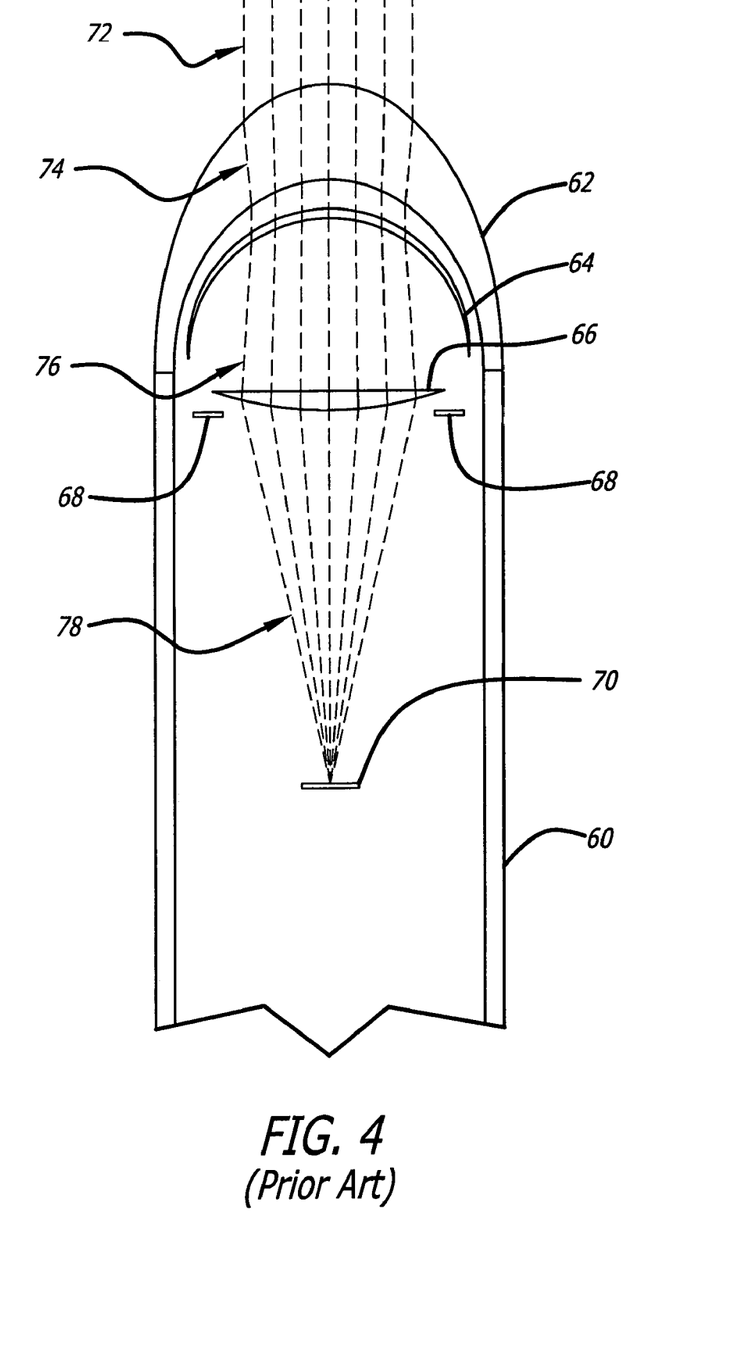
FIG. 4 is an optical diagram of a prior art conformal dome with corrector elements employed.

Reference is directed to FIG. 4, which is an optical diagram depicting the prior art approach to correcting aberrations in a conformal window where an air cavity is employed. A conformal dome 62 is fitted to the enclosure 60 and follows the same external contours as the illustrative embodiment in FIG. 2, however, the dome 62 in FIG. 4 employs a variable thickness used to somewhat reduce aberrations. Thus, the bundles of light rays 72 are refracted 74 as they pass into the dome 62 according to the exterior curvature, and then to a differing degree according to the interior surface of the dome 62 as they exit it. The light rays then pass through a corrector element 64 where they are further corrected and are then coupled 76 to a perfect lens 66. An aperture stop 68 limits the extent of the rays that are ultimately focussed 78 on focal plane 70. While the approach to correcting aberration in FIG. 4 is effective, it is considerably more complex to develop, test and more expensive to implement because of the complex element designs that are required to correct the more severe aberrations.

Figure 5A:
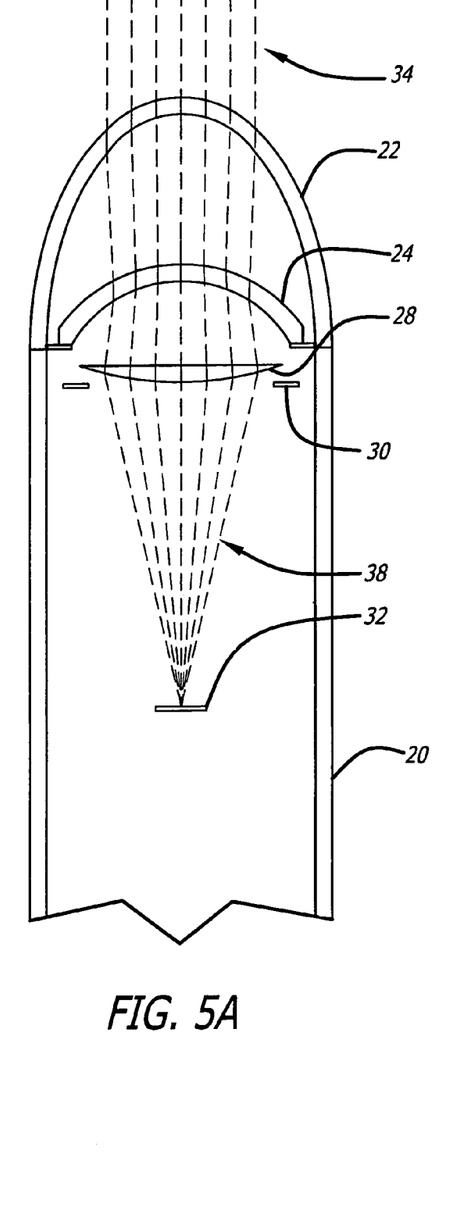
FIGS. 5A and 5B are optical diagrams depicting the geometry of a gimbal mount optical system according to an illustrative embodiment of the present invention.
Figure 5B:
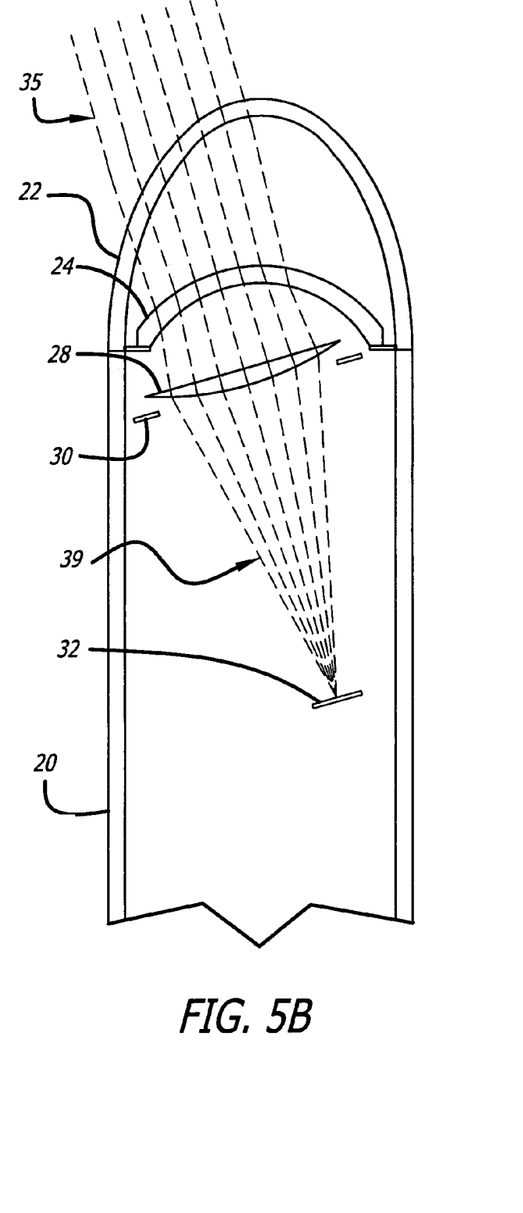

The present invention is particularly applicable to systems that employ an optical sensor supported on a gimbal mount. FIGS. 5A and 5B depict the illustrative embodiment optical system in two positions about a gimbal mount. In FIG. 5A, the housing 20, dome 22, corrector element 24, perfect lens 28 and focal plane 32 are-aligned such that the incoming bundle of light rays are aligned with the system bore sight axis. The optical sensor includes the perfect lens 28, the aperture stop 30, and focal plane sensor 32, which are fixed together and rotate about the gimbal mount in FIG. 5B, optical sensor is rotated about the gimbal mount to accept light rays 35 elsewhere in the FOR of the system. The light rays 35 are focused 39 on the sensor 32. The water filled cavity located between the dome 22 and the corrector element 24 reduces the degree of light refraction through the dome 22 such that the corrector element addresses less severe aberrations as the optical sensor is rotated about the gimbal mount. The illustrations in FIGS. 5A and 5B are for an idealized perfect lens sensor. Those skilled in the art will appreciate that a wide variety of sensors could be used in conjunction with the present invention fluid filled dome. A physically smaller sensor could be gimbal mounted inside the arch of the dome such that the look angles within the FOR of the system could exceed 180 degrees. Note that with a hemispherical dome of the prior art, the FOR would vignette at a 90 degree look angle. By applying the teachings of the present invention, the FOR can be increased while aberrations reduced and system design simplified.

Figure 6:
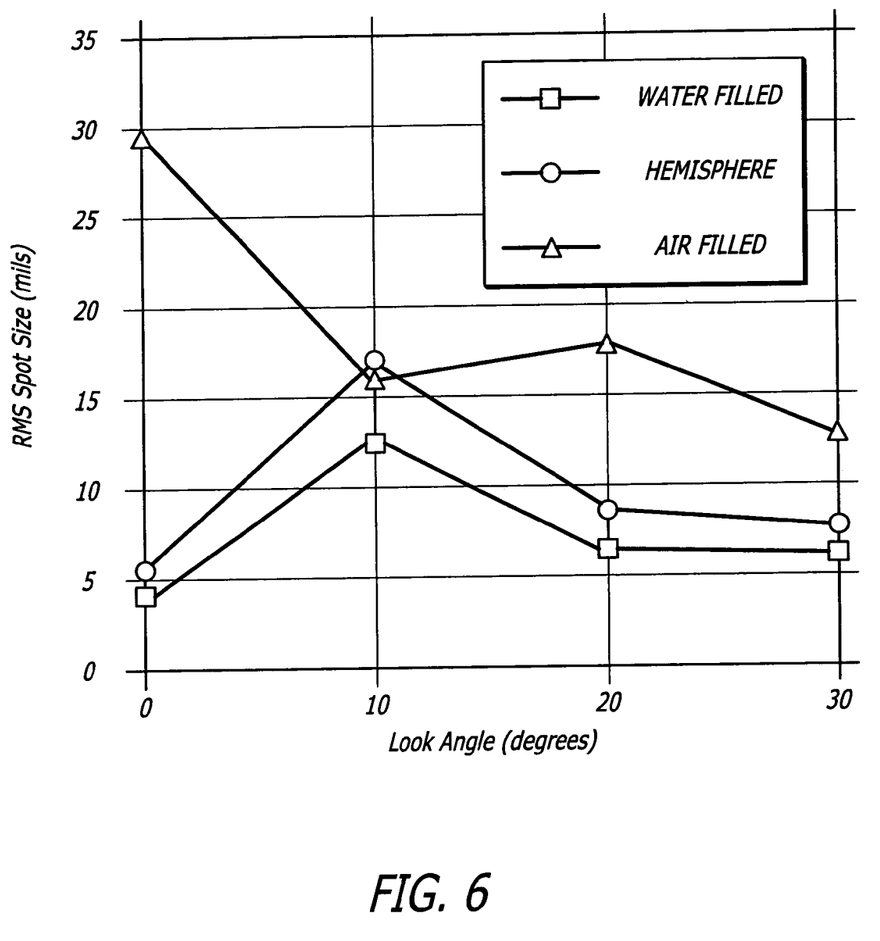
FIG. 6 is a graph comparing the performance of an illustrative embodiment of the present invention with the prior art.

Performance improvements have been verified with computer modeling of the aforementioned system designs. Reference is directed to FIG. 6, which is a graph plotting RMS image spot size as a function of look angle for three system designs. The environment used in the calculations is water with a point light source at 550 nanometers in the field of view. The 550 nanometer wavelength was selected because water has a low attenuation at this wavelength as compared to other wavelengths in the visible and adjacent bands of light. The first plot is for a water-filled ellipsoidal dome as generally illustrated in FIG. 2. The second plot is for a conventional air filled hemispherical dome design as generally depicted in FIG. 1. The third plot is for a fully corrected air filled ellipsoidal dome design as generally depicted in FIG. 4. Note that the water filled dome not only exceeds the performance of the air filled dome by a large margin, it also out performs the conventional hemispherical dome by a significant amount. Thus, a reduction in aberrations is realized by applying the teachings of the present invention.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

Accordingly,

What is claimed is:

1. A system for sensing light transmitted with reduced optical aberrations into the interior of an enclosure, comprising:
   a window disposed on the exterior surface of the enclosure for allowing light to pass into the enclosure;
   a lens disposed on the interior side of said window, defining a cavity between said window and said lens;
   a fluid disposed within said cavity, said fluid an index of refraction that minimizes any mismatch with the index of refraction of said window and
   an optical sensor disposed in the interior of the enclosure and positioned to receive light through said window and said lens.

2. The system of claim 1 wherein the exterior surface of said window is formed to a shape other than a flat plate or a spherical dome.

3. The system of claim 1 wherein the exterior surface of said window is shaped to conform to the exterior surface of said enclosure.

4. The system of claim 1 wherein the exterior surface of said window is formed to conform to a rotated conic section selected from one of an ellipse, a parabola, or a hyperbola, or is formed as a rotated ogive.

5. The system of claim 1 wherein said liquid or plasma has an index of refraction similar to the index of refraction of said window.

6. The system of claim 1 wherein said fluid is water.

7. The system of claim 6 wherein the system operates under water.

8. The system of claim 1 wherein said liquid or plasma is a gel.

9. The system of claim 1 wherein said system operates in a fluid environment and said liquid or plasma has an index of refraction similar to the index of refraction of said fluid environment.

10. The system of claim 9 wherein said fluid environment is selected from one of a bodily fluid, a hydrocarbon, a lubricant, or an industrial chemical.

11. The system of claim 1 wherein the system is a torpedo.

12. The system of claim 1 wherein said lens is a corrector element formed to offset optical aberrations caused by said window and said fluid.

13. The system of claim 1 wherein said lens is comprised of a single optical element.

14. The system of claim 1 wherein said sensor is gimbal mounted to vary the look angle of said sensor.

15. The system of claim 1 wherein said lens is formed to correct optical aberrations created by the combination of said window and said liquid or plasma, such that light is coupled to said optical sensor in a diffraction limited condition.

16. An underwater system for sensing light transmitted with reduced optical aberrations into the interior of an enclosure, comprising:
- a conformal window disposed on the exterior surface of the enclosure for allowing light to pass into the enclosure;
- a single element corrector lens disposed on the interior side of said window, defining a cavity between said window and said lens, wherein said cavity is filled with water;
- a gimbal mounted optical sensor disposed in the interior of the enclosure and positioned to receive light through said window and said lens through various look angles possible with said gimbal mount, and wherein
- said lens is formed to correct optical aberrations created by the combination of said window and said fluid, such that light is coupled to said optical sensor in a diffraction limited condition.

17. A method of implementing a system for transmitting light with reduced optical aberrations to a sensor on the interior of an enclosure, comprising the steps of:
- disposing a window on the exterior surface of the enclosure, thereby allowing light to pass into the enclosure;
- positioning a lens on the interior side of said window, thereby defining a cavity between said window and said lens;
- filling said cavity with a liquid or plasma, said liquid or plasma having an index of refraction that minimizes an mismatch with the index of refraction of said window and
- positioning the optical sensor in the interior of the enclosure to receive light through passing through said window and said lens.

18. The method of claim 17 further comprising the step of forming the exterior surface of said window to a shape other than a flat plate or a spherical dome.

19. The method of claim 17 further comprising the step of conforming the exterior surface of said window to the shape of the exterior surface of said enclosure.

20. The method of claim 17 wherein the exterior surface of said window is formed to conform to a rotated conic section selected from one of an ellipse, a parabola, or a hyperbola, or is formed as a rotated ogive.

21. The method of claim 17 wherein said liquid or plasma has an index of refraction similar to the index of refraction of said window.

22. The method of claim 17 wherein said liquid or plasma is water.

23. The method of claim 22 wherein the system operates under water.

24. The method of claim 17 wherein said liquid or plasma is a gel.

25. The method of claim 17 wherein the system operates in a fluid environment and said liquid or plasma has an index of refraction similar to the index of refraction of said fluid environment.

26. The method of claim 25 wherein said fluid environment is selected from one of a bodily fluid, a hydrocarbon, a lubricant, or an industrial chemical.

27. The method of claim 17 wherein the system is a torpedo.

28. The method of claim 17 wherein said lens is a corrector element formed to offset optical aberrations caused by said window and said liquid or plasma.

29. The method of claim 17 wherein said lens is comprised of a single optical element.

30. The method of claim 17 wherein said positioning step is accomplished with a gimbal mount, thereby varying the look angle of the sensor.

31. The method of claim 17 wherein said lens is formed to correct optical aberrations created by the combination of said window and said liquid or plasma, such that light is coupled to said optical sensor in a diffraction limited condition.

32. A system for sensing light transmitted with reduced optical aberrations into the interior of an enclosure, comprising:
- a window disposed on the exterior surface of the enclosure for allowing light to pass into the enclosure;
- a lens disposed on the interior side of said window, defining a cavity between said window and said lens;
- a liquid or plasma disposed within said cavity, said liquid or plasma having an index of refraction similar to the index of refraction of said window and
- an optical sensor disposed in the interior of the enclosure and positioned to receive light through said window and said lens.

33. A system for sensing light transmitted with reduced optical aberrations into the interior of an enclosure, comprising:
- a window disposed on the exterior surface of the enclosure for allowing light to pass into the enclosure;
- a lens disposed on the interior side of said window, defining a cavity between said window and said lens;
- a liquid or plasma disposed within said cavity, said liquid or plasma being a gel and
- an optical sensor disposed in the interior of the enclosure and positioned to receive light through said window and said lens.

34. A system for sensing light transmitted with reduced optical aberrations into the interior of an enclosure, comprising:
- a window disposed on the exterior surface of the enclosure for allowing light to pass into the enclosure;
- a lens disposed on the interior side of said window, defining a cavity between said window and said lens;
- a liquid or plasma disposed within said cavity, said system being adapted to operate in a fluid environment and said fluid having an index of refraction similar to the index of refraction of said fluid environment and
- an optical sensor disposed in the interior of the enclosure and positioned to receive light through said window and said lens.

* * * * *